(12) United States Patent
Gorsen

(10) Patent No.: US 8,092,406 B2
(45) Date of Patent: Jan. 10, 2012

(54) THERAPEUTIC BELT

(75) Inventor: Robert M. Gorsen, McLean, VA (US)

(73) Assignee: Ossur hf, Reykjavik (IS)

( * ) Notice: Subject to any disclaimer, the term of this patent is extended or adjusted under 35 U.S.C. 154(b) by 991 days.

(21) Appl. No.: 11/733,865

(22) Filed: Apr. 11, 2007

(65) Prior Publication Data
US 2007/0237808 A1 Oct. 11, 2007

Related U.S. Application Data

(60) Provisional application No. 60/790,929, filed on Apr. 11, 2006.

(51) Int. Cl.
*A61H 11/00* (2006.01)
(52) U.S. Cl. ............. 601/71; 601/79; 601/132; 601/134
(58) Field of Classification Search .................... 601/15, 601/17, 71, 79, 132, 124, 134, 136; 224/665; 2/247, 310, 460, 462, 464
See application file for complete search history.

(56) References Cited

U.S. PATENT DOCUMENTS

| | | | |
|---|---|---|---|
| 3,434,469 A | 3/1969 | Swift | |
| 3,812,862 A | 5/1974 | Bernstein | |
| 4,013,070 A * | 3/1977 | Harroff | 602/21 |
| 4,497,069 A | 2/1985 | Braunhut | |
| 4,732,140 A * | 3/1988 | Stoffregen | 601/71 |
| 4,747,399 A | 5/1988 | Glomstead | |
| 4,979,502 A * | 12/1990 | Hunt | 601/15 |
| 5,007,412 A | 4/1991 | Dewall | |
| 5,062,414 A | 11/1991 | Grim | |
| 5,144,694 A | 9/1992 | Conrad Daoud et al. | |
| 5,179,942 A | 1/1993 | Drulias et al. | |
| 5,290,307 A * | 3/1994 | Choy | 606/204 |
| 5,378,225 A | 1/1995 | Chatman, Jr. et al. | |
| 5,387,183 A | 2/1995 | Jones | |
| 5,713,840 A | 2/1998 | Brentham | |
| 5,797,955 A | 8/1998 | Walters | |
| 5,823,984 A | 10/1998 | Silverberg | |
| 5,853,378 A | 12/1998 | Modglin | |
| 5,967,998 A | 10/1999 | Modglin | |
| 6,182,288 B1 * | 2/2001 | Kibbee | 2/2.5 |
| 6,193,678 B1 * | 2/2001 | Brannon | 601/15 |

(Continued)

FOREIGN PATENT DOCUMENTS

JP 06-327707 11/1994

(Continued)

OTHER PUBLICATIONS

Extended European Search Report for EP Patent Application 07760439.5, Dec. 20, 2010.

(Continued)

*Primary Examiner* — Steven Douglas
(74) *Attorney, Agent, or Firm* — Schnader Harrison Degal & Lewis LLP

(57) ABSTRACT

A therapeutic apparatus having an expanse of material that can be adjustably wrapped around a portion of a user's body and which is securable thereon. Various therapeutic components can be attached to the material expanse in numerous positions, such that when it is secured on the user, the components direct the therapy to the area of need. Therapeutic components may include for example, pressure-creating devices, hot and cold packs and rigid support pieces. One or more flexible straps, each having an attachment mechanism to allow direct attachment to the material expanse at a plurality of positions can also be provided.

24 Claims, 2 Drawing Sheets

U.S. PATENT DOCUMENTS

| | | | |
|---|---|---|---|
| 6,233,747 B1 * | 5/2001 | Barker | 2/247 |
| 6,422,242 B1 | 7/2002 | Slautterback et al. | |
| 6,554,787 B1 * | 4/2003 | Griffin et al. | 602/74 |
| 6,711,750 B1 * | 3/2004 | Yoo | 2/338 |
| 6,755,799 B2 | 6/2004 | Toda | |
| 2001/0027282 A1 | 10/2001 | Baugh | |
| 2003/0050584 A1 | 3/2003 | Toda | |
| 2004/0167448 A1 | 8/2004 | Heffez | |

FOREIGN PATENT DOCUMENTS

| | | |
|---|---|---|
| JP | 10-155825 | 6/1998 |
| JP | 11-290372 | 10/1999 |
| JP | 2002-088517 | 3/2002 |
| JP | 2002-143205 | 5/2002 |
| JP | 2003-079747 | 3/2003 |
| JP | 2004-229781 | 8/2004 |

OTHER PUBLICATIONS

Office Action dated May 6, 2010 for Chinese Patent Application No. 200780012826.8.

International Search Report and Written Opinion dated Jan. 4, 2008 for PCT Patent Application PCT/US07/66375.

* cited by examiner

THERAPEUTIC BELT

This application is based on, and claims priority to, provisional application having Ser. No. 60/790,929, having a filing date of Apr. 11, 2006 and entitled Medical Support Belt.

FIELD OF THE INVENTION

The invention relates to therapeutic systems for use on external surfaces of the body.

BACKGROUND OF THE INVENTION

Rib belts or abdominal supports exist to provide individuals with extra support needed due to weakened muscles, surgical procedures or back pain for example. Maternity supports also exist to reduce muscle strain and low back pain associated pregnancy. Rib belts may also provide stable support to injured ribs, limit chest expansion and help promote healing.

Back supports can be designed to provide pressure to the back by use of laces, such as in corset-type support. Traditional designs are limited in that they cannot direct pressure to specific points, as may be needed.

Back supports may also incorporate metal stays to provide the appropriate rigidity and support for the back. Rigid back supports are limited in that they may not conform to a large variety of body types unless they are custom formed, which increases their cost.

Existing back supports are also limited in their adjustability, and therefore, may not provide an optimum fit or therapeutic value. Accordingly, a need exists for a support or belt that can be fitted to numerous body types, can provide directed pressure and can incorporate various components to provide the maximum therapeutic benefit.

SUMMARY OF THE INVENTION

A therapeutic apparatus is disclosed having an expanse of material that can be adjustably wrapped around a portion of a user's body and which is securable thereon. The material expanse is thus generally in the form of a belt for many applications. Various therapeutic components can be attached to the belt in numerous positions, such that when the belt is secured on the user, the components direct the therapy to the area of need. Therapeutic components may include for example, pressure-creating devices, hot and cold packs and rigid support pieces. The adjustability of the component location provides an apparatus that can direct therapeutic effects very accurately. A securable band may be provided to more securely hold components on the material expanse. The band can increase pressure and effectiveness of the therapeutic components.

One or more flexible straps, each having an attachment mechanism to allow direct attachment to the material expanse at a plurality of positions can also be provided. This allows the apparatus to conform to a wide variety of body-types and sizes.

DETAILED DESCRIPTION OF THE INVENTION

Figure 1:
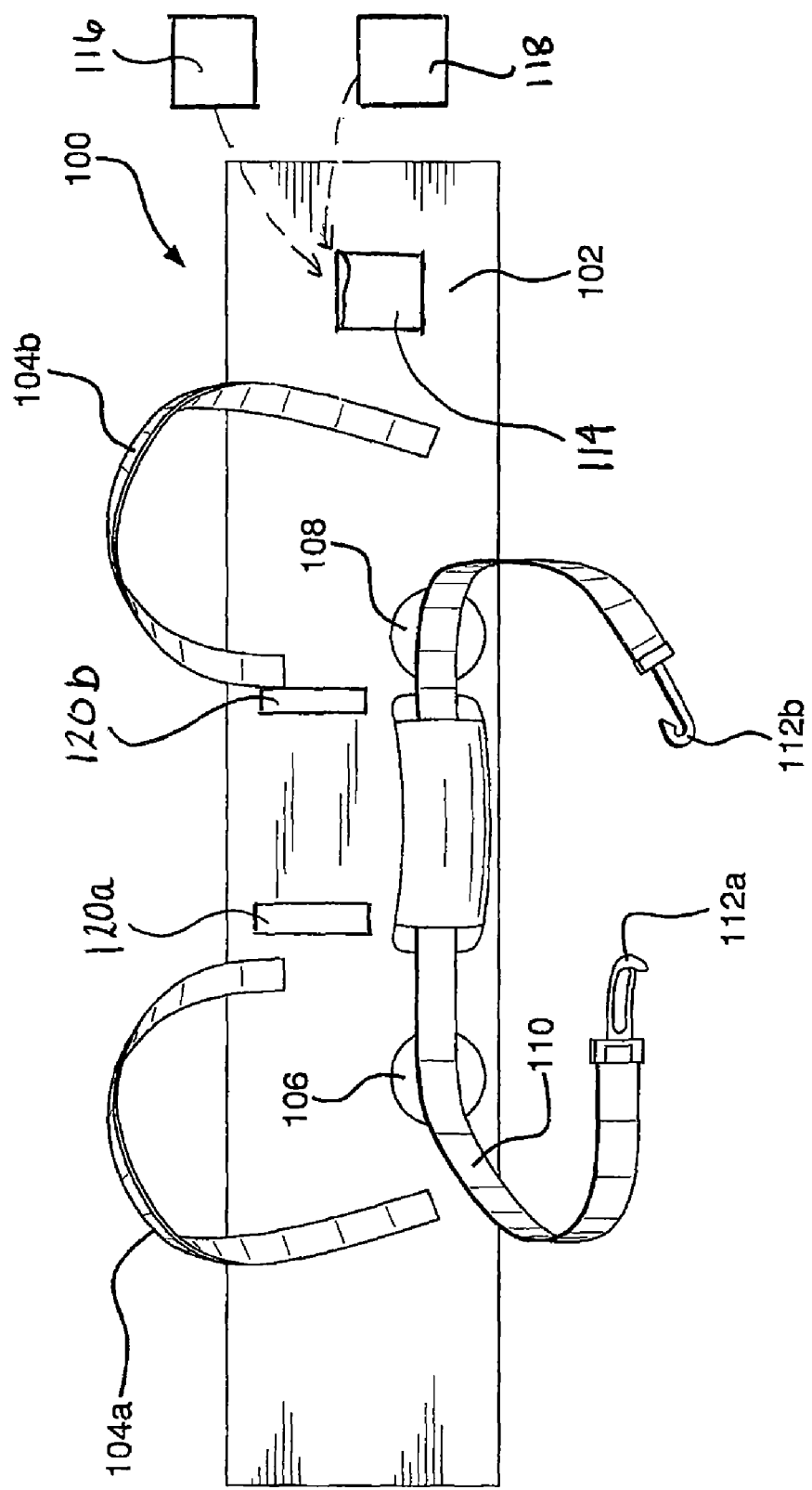
FIG. 1 depicts a therapeutic apparatus according to an illustrative embodiment of the invention.
Figure 2:
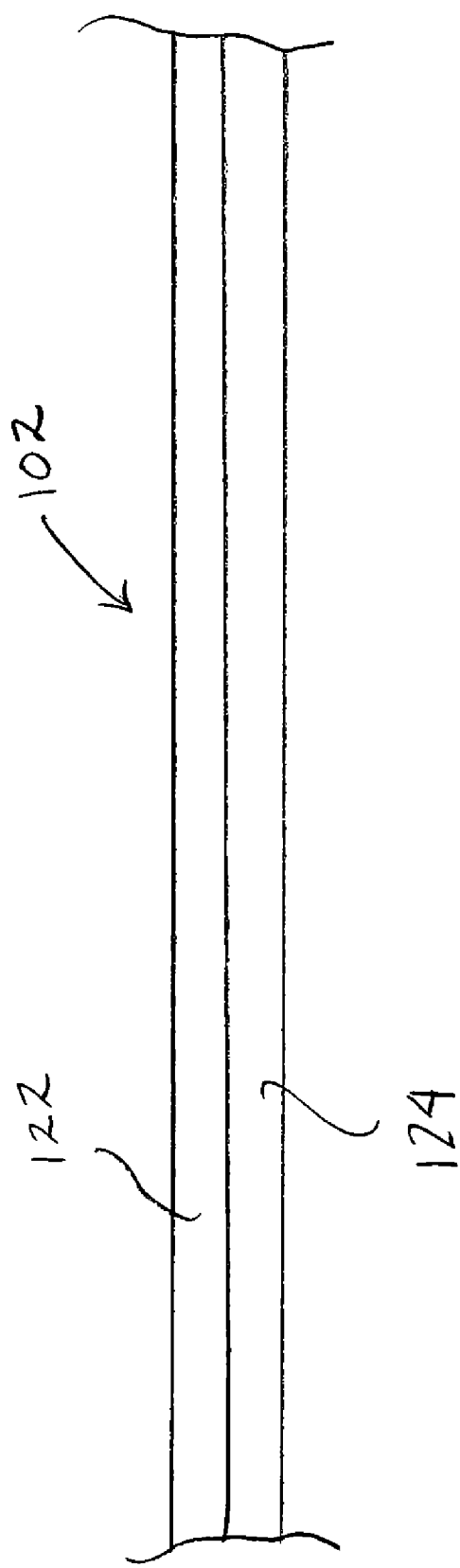
FIG. 2 depicts a cross-section of a portion of a therapeutic apparatus according to an illustrative embodiment of the invention.

FIG. 1 depicts a therapeutic apparatus 100 according to an illustrative embodiment of the invention. Therapeutic apparatus 100 includes a material expanse 102, in the form of a belt. As will be described more fully below, belt 102 can be made of various materials, and in some embodiments can be in the form of, or considered to be a brace. The material is preferably a soft, flexible synthetic material, however, numerous types of material may be used. Natural fibers, such as cotton may provide desirable breathability. Machine washable materials are also beneficial. Materials with some stretch, such as provided by the inclusion of Lycra®, may provide additional support or pressure. In an illustrative embodiment of the invention, the belt is made of neoprene or other synthetic rubber material. The belt may comprise two or more layered materials, each providing a different function or merely used for appearance. For example, materials may address moisture issues, chafing problems, etc. Microfiber materials, wicking materials, etc. may be suitable for use as a layer. FIG. 2 depicts a portion of a material expanse 102 having a layer of flexible material 122 and a layer of one of a hook or loop material 124 attached to it.

Material expanse 102 may provide a user with support to a particular body part or area, such as when worn around the torso to provide back support. Material expanse 102, however, may merely be the foundation onto which one or more therapeutic components are attached, without supplying support or pressure on its own.

Illustrative therapeutic apparatus 100 has straps 104a, 104b that are attachable at a plurality of positions on material expanse 102. Straps 104a, 104b can be disposed over the shoulders of a wearer, for example if the apparatus is used to direct therapy to the back. Straps 102 can be readily adjusted with respect to length and position around an individual's body by detaching and re-attaching one or both ends of the straps to a suitable location on the belt. This allows the apparatus to be used on individuals with a wide variety of body types. Characteristics of straps 104a, 104b, such as their number, size and material, will vary depending on the application of the therapeutic apparatus.

One or more attachable therapeutic components can be provided with the therapeutic apparatus. FIG. 1 shows pressure-creating components 106, 108 in the form of balls. Pressure-creating components 106, 108 are depicted with a securable band 110 disposed over them. Band 110 has fasteners 112a, 112b to secure the band around pressure-creating components 106, 108 and thus apply pressure to the desired body areas. Band 110 is depicted with fasteners 112a, 112b to secure band 110 over belt 102. Fasteners 112a, 112b are shown as spring-loaded clasps. Other forms of closure can also be used, such as hook and loop materials. Band 110 may also be comprised of elastic for comfort and/or to accommodate various waist sizes.

Detachable pockets 114 may be included, into which hot or cold packs 116 can be inserted, allowing the pocket insert to target a specific location. Devices for providing vibration therapy 118 can also be inserted in pockets. The belt with detachable pockets is an improvement over devices that have fixed pocket locations.

It is noted that items such as hot and cold packs, and vibration devices can be attached to the belt by means other than by inserting them into pockets. For example, they may be more directly attached by applying Velcro® to the packs or devices so they can adhere to the belt.

Detachable panels 120a,b or stays can also be provided to create rigidity and support as and where needed. Although the term "stay" usually refers to a thin strip and a "panel" may refer to a wider strip, the term "panel" will be used herein to encompass both thin and wider components. Preferably the panels have a rectangular shape and can be disposed vertically or horizontally with respect to the belt. Angular orientations are also possible. In an exemplary embodiment of the invention, the panels are substantially rectangular with rounded edges to minimize irritation and wear to materials. Panels can be flat or else contoured for particular applications. Panels can be attached at locations throughout the belt to provide full support, or be located only in the back to allow flexing at the waist, or at other locations as needed. Again, the ability to locate the components in very specific places, and to do so with ease, renders embodiments of the apparatus superior in many respects to existing products.

In an illustrative embodiment of the invention, the panels are comprised of a rigid material such as wood, plastic or metal for example, with a hook or loop material on at least one side. The hook or loop material may cover an entire side of the rigid piece or a portion thereof. The hook or loop material can be permanently affixed to the rigid material, such as by glue or bonding. It may also be in the form of a cover, which is either permanently disposed over the rigid piece or removable. The panels can have a hook or loop material on one side or both. If on both sides, hook or loop material on one side, such as that which faces the user, allows the panel to be secured to the belt and the other side secured to the band that may be placed over the panels to secure the belt and therapeutic components in place.

Components can be made to be stacked. For example, if heat is needed where a pressure point is desired, a pocket can be attached to the main belt and a pressure component such as a ball can be stacked on top of it.

Preferably a Velcro®-type material is used to attach the components to the belt. This allows the components to be located at any position on the belt and easily relocated as necessary. Other forms of attachment are within the spirit and scope of the invention and can be used with or without a Velcro®-type material (hook and loop or other material having complementary parts, which adhere to each other when pressed together). For example, a belt can be provided with a series of holes into which buttons on the components can be inserted or vice versa. This may be desirable if, for example, the shoulder straps need a stronger attachment to the belt than can be provided by hook and loop materials. The advantage of a Velcro®-type system, however, is the ability to place components in substantially unlimited locations and the smoothness at the attachment locations, which reduces unwanted pressure points. In the Velcro®-type system, however, the Velcro® or other similar material need not be disposed throughout the apparatus, but only in areas where components may need to be attached.

Thus far, the invention has been presented as a back support. It is noted, however, that the general concept of an adjustable belt with detachable components can be used for other parts of the body. The belt can be used to apply heat or cold to various body parts, put pressure on wounds, etc. It can also be used as a splint, for example on an arm, leg or finger.

The invention may be embodied in a variety of ways, for example, as a system, method or apparatus. An illustrative embodiment of the invention provides a therapy method in which an expanse of material is provided onto which one or more therapeutic components can be attached at a variety of positions. The nature of the therapy needed is determined and the associated therapeutic components are identified. The components are then directly attached to the material expanse. For example, the material expanse can be a hook-type material and the therapeutic components can have a loop-type material affixed to, or an integral part of them.

The method includes attaching therapeutic components on the material expanse in positions where they will provide a desired therapy to one or more selected body areas. The material expanse is wrapped around a body part of the user, or otherwise applied to the user, such that the therapeutic components are positioned on the user to provide the desired therapy. The therapeutic components may be secured to the belt either before or after it is positioned on the user. In most instances, the components can be more accurately positioned if they are placed on the belt after the belt is applied to the user. The material expanse with the attached components can then be secured to the user, such as by a securable band.

A further illustrative method includes providing one or more flexible straps and attaching them to the material expanse at desired positions to enable the therapeutic apparatus to be positioned on the user to provide the necessary therapy.

Yet another illustrative embodiment of the inventive method includes stacking two or more of the therapeutic components on the material expanse.

While the invention has been described by illustrative embodiments, additional advantages and modifications will occur to those skilled in the art. Therefore, the invention in its broader aspects is not limited to specific details shown and described herein. Modifications, for example, to the types of components and materials used, may be made without departing from the spirit and scope of the invention. Accordingly, it is intended that the invention not be limited to the specific illustrative embodiments, but be interpreted within the full spirit and scope of the claimed embodiments and their equivalents.

The invention claimed is:

1. A therapeutic apparatus comprising:
    an elongated expanse of material adjustably wrappable around a portion of a user's body and securable thereon;
    two or more adjustably locatable therapeutic components, each having an attachment mechanism located thereon to allow direct attachment of each therapeutic component to the material expanse at a plurality of selected arbitrary positions on the outside of the material expanse;
    a single securable band, securable over one of the two or more therapeutic components and also securable over two or more of the two or more therapeutic components as selected by the user and capable of increasing pressure of the therapeutic components on the user; and
    one or more flexible straps each having an attachment mechanism located thereon to allow direct attachment of the straps to the material expanse at a plurality of positions configurable to conform to a variety of body types and sizes.

2. The therapeutic apparatus of claim 1 wherein at least one of the one or more of the two or more therapeutic components includes one or more pressure-creating components.

3. The therapeutic apparatus of claim 1 further comprising one or more pockets into which therapeutic devices can be inserted the pockets having an attachment mechanism to allow direct attachment to the material expanse at a plurality of positions on the outside of the belt.

4. The therapeutic apparatus of claim 1 wherein at least one of the one or more therapeutic devices includes at least one vibration device.

5. The therapeutic apparatus of claim 1 wherein at least one of the one or more therapeutic devices includes at least one temperature varying device.

6. The therapeutic apparatus of claim 1 wherein the attachment mechanism of at least one of the therapeutic components includes hook and loop materials.

7. The therapeutic apparatus of claim 1 further comprising:
one or more panels, each having an attachment mechanism to allow direct attachment to the material expanse at a plurality of positions.

8. The therapeutic apparatus of claim 1 wherein two or more of the two or more therapeutic components are stackable on the material expanse.

9. The therapeutic apparatus of claim 1 wherein the material expanse provides back support to the user.

10. The therapeutic apparatus of claim 1 wherein the material expanse comprises a flexible base material having one of a hook or loop material attached thereto and extending over at least a portion of one or more surfaces of the material expanse.

11. The therapeutic apparatus of claim 10 wherein the base material is a synthetic rubber.

12. A therapeutic apparatus comprising:
an expanse of material adjustably wrappable around a portion of a user's body and securable thereon;
one or more panels, each having an attachment mechanism to allow direct attachment to the outside of the material expanse at a plurality of positions;
one or more pressure-creating components, each having an attachment mechanism to allow direct attachment to the outside of the material expanse at a plurality of positions;
one or more flexible straps each having an attachment mechanism to allow direct attachment to the material expanse at a plurality of positions wherein the straps are configured to be disposed over the shoulders of a wearer; and
a band securable over at least one of the one or more panels and one or more pressure-creating components;
wherein the attachment mechanisms include hook and loop materials.

13. The therapeutic apparatus of claim 12 further comprising:
one or more pockets into which therapeutic devices can be inserted, each pocket having an attachment mechanism to allow direct attachment to the material expanse at a plurality of positions.

14. The therapeutic apparatus of claim 12 wherein two or more of the one or more therapeutic components are stackable on the material expanse.

15. A therapy method comprising:
providing a therapeutic apparatus according to claim 1;
choosing one or more therapeutic components;
directly attaching the one or more therapeutic components to the material expanse in positions on the material expanse to provide a desired therapy to one or more selected body areas;
wrapping the material expanse around a portion of a user's body such that the therapeutic components are positioned at the selected body areas;
securing the material expanse to the user; and
securing a band over one or more therapeutic components to increase pressure of the therapeutic component against the body.

16. The method of claim 15 wherein the chosen therapeutic components include one or more pressure-creating components.

17. The method of claim 15 wherein the chosen therapeutic components include one or more pockets into which therapeutic devices can be inserted.

18. The method of claim 15 wherein the therapeutic components are attached by using hook and loop materials.

19. The method of claim 15 wherein the chosen therapeutic components include one or more panels.

20. The method of claim 15 further comprising:
stacking two or more of the two or more therapeutic components on the material expanse.

21. The method of claim 15 further comprising:
securing a band over the material expanse and therapeutic components.

22. The therapeutic apparatus of claim 1 wherein the straps are configured to be disposed over the shoulders of a wearer.

23. The therapeutic apparatus of claim 1 wherein the straps are configured to be adjusted with respect to length and position around an individual's body.

24. The therapeutic apparatus of claim 1 wherein both ends of at least one flexible strap are removably attachable to the material expanse at a plurality of positions.

* * * * *